United States Patent
Akagi et al.

(10) Patent No.: US 12,409,202 B2
(45) Date of Patent: *Sep. 9, 2025

(54) AUTONOMIC NERVE REGULATOR AND COGNITIVE FUNCTION IMPROVER

(71) Applicant: FUJICCO CO., LTD., Hyogo (JP)

(72) Inventors: Ryota Akagi, Kobe (JP); Toshinari Maruo, Kobe (JP); Narumi Mori, Kobe (JP); Toshio Suzuki, Kobe (JP)

(73) Assignee: FUJICCO CO., LTD., Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/876,955

(22) Filed: Jul. 29, 2022

(65) Prior Publication Data

US 2023/0050805 A1  Feb. 16, 2023

(30) Foreign Application Priority Data

Jul. 30, 2021 (JP) .................................. 2021-125497

(51) Int. Cl.
*A61K 36/48* (2006.01)
*A61K 9/20* (2006.01)
*A61K 9/48* (2006.01)
*A61P 25/28* (2006.01)

(52) U.S. Cl.
CPC ............ *A61K 36/48* (2013.01); *A61K 9/2009* (2013.01); *A61K 9/2013* (2013.01); *A61K 9/2054* (2013.01); *A61K 9/2059* (2013.01); *A61K 9/4858* (2013.01); *A61K 9/4875* (2013.01); *A61P 25/28* (2018.01)

(58) Field of Classification Search
CPC .... A61K 36/48; A61K 9/2009; A61K 9/2013; A61K 9/2054; A61K 9/2059; A61K 9/4858; A61K 9/4875; A61P 25/28
See application file for complete search history.

(56) References Cited

U.S. PATENT DOCUMENTS

| | | | |
|---|---|---|---|
| 7,125,911 B2 | 10/2006 | Nagashima et al. | |
| 2002/0151600 A1 | 10/2002 | Nagashima et al. | |
| 2004/0039065 A1 | 2/2004 | Nagashima et al. | |
| 2004/0048933 A1 | 3/2004 | Nagashima et al. | |
| 2009/0214681 A1* | 8/2009 | Wu ....................... | A61K 36/48 424/757 |
| 2015/0209317 A1 | 7/2015 | Ceddia et al. | |

FOREIGN PATENT DOCUMENTS

| | | |
|---|---|---|
| CN | 106177223 | 12/2016 |
| JP | 11-299452 | 11/1999 |
| JP | 2021-128689 | 5/2002 |
| JP | 2005261237 A * | 9/2005 |
| JP | 4669077 | 4/2011 |
| JP | 2013-35786 | 2/2013 |
| JP | 2013-95756 | 5/2013 |
| JP | 2015110536 A * | 6/2015 |
| JP | 2016183121 A * | 10/2016 |
| JP | 2019-206566 | 12/2019 |
| WO | 01/58435 | 8/2001 |
| WO | 2014/054174 | 4/2014 |
| WO | 2018/174294 | 9/2018 |
| WO | 2019/054461 | 3/2019 |

OTHER PUBLICATIONS

Jeong et al. An investigation into the ameliorating effect of black soybean extract on learning and memory impairment with assessment of neuroprotective effects. BMC Complementary and Alternative Medicine 2014, 14:482 (Year: 2014).*
Jeong et al. Black Soybean Extract Protects Against TMT-Induced Cognitive Defects in Mice. J Med Food 17 (1) 2014, 83-91. (Year: 2014).*
Ganesan et al. A Critical Review on Polyphenols and Health Benefits of Black Soybeans. Nutrients 2017, 9, 17 pages. (Year: 2017).*
O'Brian et al., Soybean Seed Coats: A Source of Ingredients for Potential Human Health Benefits—A Review of the Literature. Journal of Food Research; vol. 3, No. 6; 2014, 188-201. (Year: 2014).*
"Sensing of stress and fatigue and its evaluation technique", Technical Information Society of Japan, published Oct. 31, 2019, pp. 338-339 (with partial English translation).
Office Action issued Apr. 7, 2022 in corresponding Japanese Patent Application No. 2020-094976, with machine English translation, 9 pages.
Decision of Refusal issued Aug. 23, 2022 in corresponding Japanese Patent Application No. 2020-094976, with machine English translation, 12 pages.
Office Action issued Jul. 25, 2023 in corresponding Japanese Application No. 2022-186286, with English translation.
Office Action (non-final) dated Jun. 12, 2025 issued in U.S. Appl. No. 17/898,960.

* cited by examiner

*Primary Examiner* — Robert A Wax
*Assistant Examiner* — Olga V. Tcherkasskaya
(74) *Attorney, Agent, or Firm* — Wenderoth, Lind & Ponack, L.L.P.

(57) ABSTRACT

A composition having an autonomic nervous system modulatory function-improving effect or an effect for suppressing a decrease of an autonomic nervous system modulatory function, and a composition having a cognitive function-improving effect or an effect for suppressing a decrease of a cognitive function. A composition for modulating an autonomic nervous system, including a black soybean seed coat extract, a composition for improving a cognitive function, including a black soybean seed coat extract, and use of a black soybean seed coat extract in production of a composition for modulating an autonomic nervous system or a composition for improving a cognitive function.

8 Claims, 2 Drawing Sheets

[FIG. 1]

[FLOW CHART OF SUBJECT]

AUTONOMIC NERVE REGULATOR AND COGNITIVE FUNCTION IMPROVER

TECHNICAL FIELD

The present invention relates to an oral composition suitably used for modulating an autonomic nervous system function. The present invention also relates to an oral composition suitably used for improving a cognitive function.

BACKGROUND ART

According to Japanese Society of Fatigue Science, "fatigue" is defined as "a reduced capacity for physical activity associated with unique uneasiness and a desire for rest, caused by excessive physical and mental activities or illness". In recent years, in addition to stress caused by mental tension due to human relations or the like, long hours of desk work, in particular, visual display terminal (VDT) work using a display device such as a computer display has increased mental fatigue. Such mental fatigue and stress are said to be closely related to the autonomic nervous function.

The autonomic nervous system is composed of sympathetic nerves and parasympathetic nerves, which have an antagonistic action to each other. The physical and mental health is maintained by balancing the both nerves. In a normal state, sympathetic activity becomes dominant during physical activity, and then the whole body gets into a state of tension. Conversely, when parasympathetic activity is dominant, physical tension is released and the whole body gets into a relaxed state. However, when a stress state continues for a long time, the balance in the autonomic nervous system is disturbed, and the tension state of sympathetic nerves continues, thereby parasympathetic nerves become chronically difficult to work, resulting in autonomic nervous system imbalance. As a result, a brain responsible for the autonomic nervous system is not sufficiently recovered, and thereby, mental anxiety and a decrease in cognitive function are caused to not only hinder daily life but also increase the risk of developing depression (Sensing of stress and fatigue and its evaluation technique", written by Technical Information Society of Japan, published on Oct. 31, 2019, pp. 338 to 339).

Thus, there is an increasing demand for drugs and food and beverage products that modulate the autonomic nervous function to effectively improve symptoms such as a reduced working memory ability and mood disorder associated with mental fatigue and stress.

Methods for enhancing an autonomic nervous system modulatory function are studied, and for example, use of cedrol (WO 2001/058435 A), an asparagus pseudo-leaf (JP 4669077 B2), tiliroside (JP 2013-35786 A), β-eudesmol (JP 2013-95756 A), or eleutheroside E (WO 2018/174294 A) is suggested. In addition, as a method for enhancing a cognitive function, use of rosmarinic acid (JP 2019-206566 A) or cacao polyphenol (WO 2019/05446 A) is suggested.

However, improvement of an autonomic nervous system modulatory function and a cognitive function by a black soybean seed coat extract has not been reported.

SUMMARY OF THE INVENTION

Problems to be Solved by the Invention

An object of the present invention is to provide a composition capable of improving an autonomic nervous system modulatory function or suppressing a decrease of an autonomic nervous system modulatory function. Another object of the present invention is to provide a composition capable of improving a cognitive function or suppressing a decrease of a cognitive function.

Solution for the Problems

The present inventors extensively studied for achieving the above-mentioned objects, and resultantly found that ingestion of a black soybean seed coat extract improved an autonomic nervous system modulatory function in a subject when the subject was subjected to a mental fatigue load. Thus ingestion of a black soybean seed coat extract results in improvement of an autonomic nervous system modulatory function, and thereby fatigue is alleviated. Further, the present inventors found that ingestion of a black soybean seed coat extract improved a cognitive function in a subject when the subject was subjected to a mental fatigue load. Thus ingestion of a black soybean seed coat extract results in improvement of an autonomic nervous system modulatory function and then alleviation of fatigue, and thereby a decrease of a cognitive function caused by the mental fatigue load is suppressed.

The present invention relates to (1) to (7) exemplified below.

(1) A composition for modulating an autonomic nervous system, comprising a black soybean seed coat extract.
(2) The composition according to (1), which is used for prevention or improvement of mental fatigue, drowsiness, eyestrain, or shoulder stiffness.
(3) A composition for improving a cognitive function, comprising a black soybean seed coat extract.
(4) The composition according to any one of (1) to (3), wherein the composition exerts an effect on a subject after the subject was subjected to a mental fatigue load.
(5) The composition according to any one of (1) to (4), wherein the black soybean seed coat extract is an acidic extract of black soybean seed coat.
(6) The composition according to any one of (1) to (5), which is an oral composition.
(7) The composition according to any one of (1) to (5), which is a food or beverage composition.
(8) Use of a black soybean seed coat extract in production of a composition for modulating an autonomic nervous system or a composition for improving a cognitive function.

Effects of the Invention

According to the present invention, it is possible to provide a new composition that improves an autonomic nervous system modulatory function or suppresses a decrease of an autonomic nervous system modulatory function. In addition, according to the present invention, it is possible to provide a new composition that improves a cognitive function or suppresses a decrease of a cognitive function. In addition, the composition of the present invention can be used for imparting at least one of the ability to improve an autonomic nervous system modulatory function, the ability to suppress a decrease of an autonomic nervous system modulatory function, the ability to improve a cognitive function, or the ability to suppress a decrease of a cognitive function to an oral composition or a food or beverage composition. That is, according to the present invention, it is possible to prepare and provide composition or a food or beverage composition (e.g. oral pharmaceuticals, oral quasi-pharmaceutical products, food and drink products, etc.) having an excellent effect of improving an autonomic nervous system modulatory function or suppressing a decrease of an autonomic nervous system modulatory function, or having an excellent effect of improving a cognitive function or suppressing a decrease of a cognitive function.

MODES FOR CARRYING OUT THE INVENTION

Figure 1:
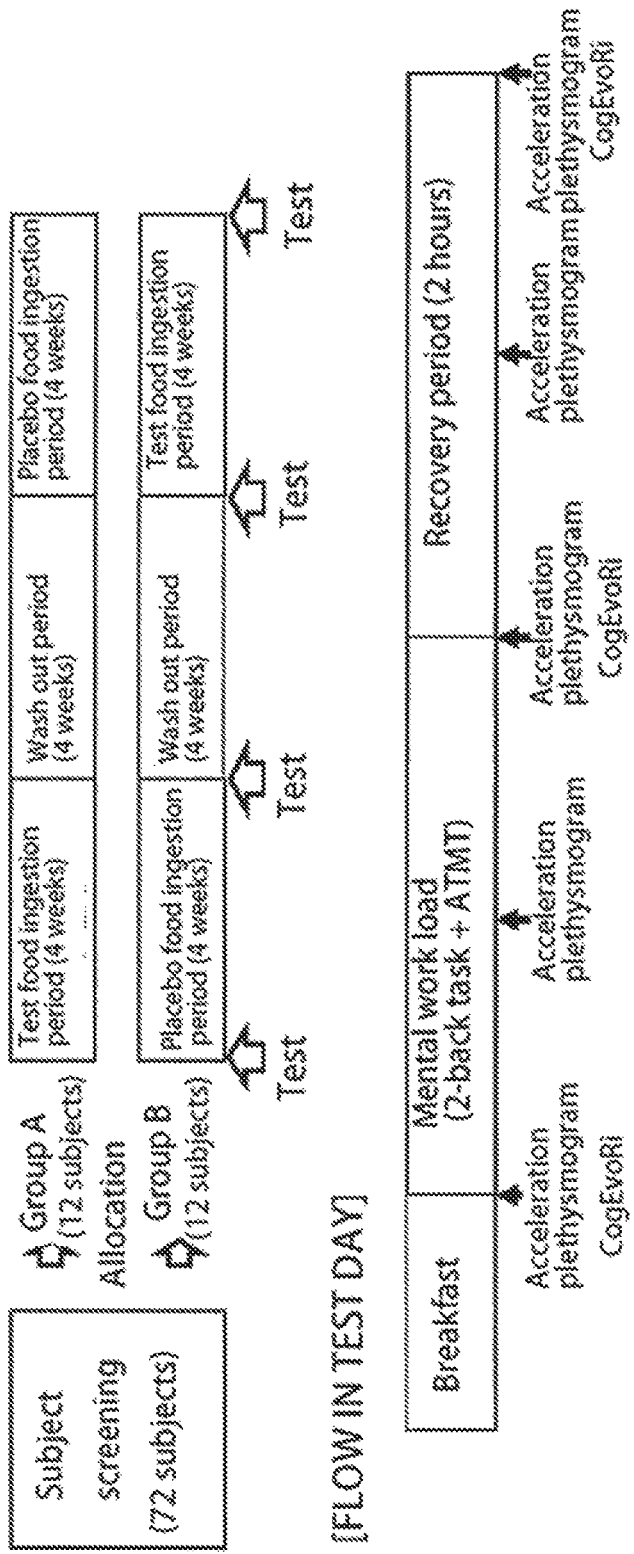
FIG. 1 is a diagram showing a test design.

Hereinafter, the composition for modulating an autonomic nervous system or the composition for improving a cognitive function of the present invention, and a method for using or producing a black soybean seed coat extract will be explained with reference to embodiments to which the present invention is not limited.

[1] Composition for Modulating Autonomic Nervous System or Composition for Improving Cognitive Function The composition for modulating an autonomic nervous system or the composition for improving a cognitive function of the present invention (hereinafter, also simply referred to as "the present composition") is characterized by containing an extract of a black soybean seed coat as an active ingredient.

As used herein, the modulation of an autonomic nervous system includes enhancement of sympathetic activity, suppression of enhanced sympathetic activity, suppression of sympathetic activity, enhancement of parasympathetic activity, suppression of enhanced parasympathetic activity, and suppression of parasympathetic activity, and preferably refers to enhancement of sympathetic activity. For example, modulating an autonomic nervous system means preventing the onset of, or alleviating or relieving various symptoms of unidentified clinical syndrome, including general malaise, easy fatigability, shortness of breath, palpitation, limb numbness, shoulder stiffness, eyestrain, headache, dizziness, hot flashes, irritation, anxiety, loss of appetite, malaise, drowsiness, insomnia, and poor concentration, which are autonomic nervous system-related diseases and symptoms caused by enhanced sympathetic activity during physical activity and enhanced parasympathetic activity during rest, or imbalance between sympathetic and parasympathetic nerves in the autonomic nervous system. The autonomic nervous system can be measured by a method known in the art, and may be measured by, for example, frequency analysis of a finger acceleration plethysmogram, heart rate variability analysis using an electrocardiogram, or the like.

As used herein, the improvement of a cognitive function means improving or maintaining at least one of a planning ability, a memory ability, an attention ability, a space recognition ability, or an orientation function. For example, the memory ability is an ability to remember things without forgetting and take out them when necessary. For example, the attention ability is an ability to appropriately and timely select information taken through the five senses. For example, the planning ability is an ability to predict a situation and consider and execute an optimal plan. For example, the orientation function is an ability to grasp basic situations such as a time and date, a place where you are, and the like. For example, the space recognition ability is an ability to quickly and accurately grasp states and a relationship of objects occupying a space. For example, the improvement of a cognitive function means improving or maintaining these abilities. The cognitive function can be measured by a method known in the art, and may be measured by, for example, "CogEvo Ri" (manufactured by Total Brain Care Co., Ltd.) for cognitive function measurement composed of 8 tasks which was developed under the supervision of RIKEN, "CogHealth" (manufactured by Cogstate Ltd) which was developed mainly by the University of Melbourne, Australia, or the like.

The black soybeans used in the present invention are black seeds (black soybeans) of a short-day annual herbaceous plant belonging to the family Fabaceae, genus *Glycine*, *Glycine max* (L.) Merrill. Examples of black soybean cultivars include Chuuseihikarikuro, Tokachikuro, Iwaikuro, Tamadaikoku, Tambaguro, Shinanokuro, and Gankui. In the present invention, any cultivar of black soybean may be used.

The black soybeans can be separated into seed coats and embryos (cotyledons and embryonic axes) by, for example, a separating machine or the like. In the present invention, the black soybean seed coats obtained by the separation can be used as raw materials for processing. For the processing treatment, the black soybean seed coats may be used directly after the separation (in a raw or dried state), or may be used after being ground or pulverized (in a ground, pulverized, or powdery state).

For extraction from the black soybean seed coats, a commonly used method can be used. Examples of such a method include, but not limited to, a method comprising immersing raw or dried black soybean seed coats (as they are, or in a coarse powdery, fine cut, ground, or pulverized state) in an water-soluble solvent, an extraction method comprising stirring as necessary, and a percolation method. Conditions of temperature for the extraction are not particularly limited. The extraction may be performed under any condition of low temperature, room temperature, or heating (including high temperature). A heating condition (including high temperature) is preferred for the reason that extraction efficiency is increased. Specifically, in the case of extraction with a hydrous lower alcohol as described later, the temperature condition is a temperature of 30° C. or higher, preferably 40° C. to 60° C., and when the extraction is performed under such a temperature condition for 60 minutes or more, preferably for about 90 minutes to 120 minutes, the desired black soybean seed coat component (extract) is sufficiently extracted. In the case of extraction with an acidic aqueous solution, the temperature condition is a temperature of 50° C. or higher, preferably 50° C. to 80° C., and for example, the extraction is performed under such a temperature condition for 10 minutes or more, preferably for about 20 minutes to 120 minutes.

Examples of the water-soluble solvent used for the extraction include, but not particularly limited to, water, a lower alcohol, and a mixture thereof. Examples of the lower alcohol include lower alcohols having 1 to 4 carbon atoms such as methanol, ethanol, propanol, isopropyl alcohol, and butanol. A preferable example of the lower alcohol is ethanol. Preferable examples of the water-soluble solvent include water and a hydrous lower alcohol (particularly hydrous ethanol), and more preferably water which is easy to handle at the time of extraction or purification. When a hydrous lower alcohol is used as a solvent, the amount of the lower alcohol contained in the solvent is preferably 80% by volume or less.

The water-soluble solvent used for the extraction is preferably adjusted to acidic pH for the purpose of enhancing the stability of the black soybean seed coat component (extract) and the like. Examples of the pH of the water-soluble solvent include, but not limited to, preferably about pH 1 to 4, and more preferably pH 1 to 2. In order to adjust the water-soluble solvent to pH in the above-mentioned range, a suitable acidic substance such as an organic acid or an inorganic acid can be usually used.

Specific examples of the acidic substance include inorganic acids such as hydrochloric acid, sulfuric acid, nitric acid, phosphoric acid and boric acid, and organic acids such as methanesulfonic acid, benzenesulfonic acid, p-toluenesulfonic acid, 10-camphorsulfonic acid, fluorosulfonic acid (these are sulfonic acids), formic acid, acetic acid, citric acid, oxalic acid (these are carboxylic acids). Preferably, an acid having a sulfo group is used. Specific examples of the acid having a sulfo group include sulfuric acid, methanesulfonic acid, benzenesulfonic acid, p-toluenesulfonic acid, 10-camphorsulfonic acid, and fluorosulfonic acid. Among them, sulfuric acid is preferable. When the extraction is performed in the presence of an acid having a sulfo group under a low temperature-heating condition at 50 to 80° C., a polyphenol composition containing a high proportion of low-polymerization degree proanthocyanidins and a low proportion of cyanidin 3-glucoside is produced. The normality of the acid in the water-soluble solvent is not particularly limited as long as the water-soluble solvent is in the above-mentioned pH range. The water-soluble solvent may contain preferably 0.01 to 0.5 N, more preferably 0.03 to 0.5 N of the acidic substance.

The extract thus obtained may be used as it is as the present composition, or may be further purified by removal of solids by filtration, coprecipitation or centrifugation, activated carbon treatment, or adsorption treatment. For example, for the purpose of increasing the concentration of polyphenol in the black soybean seed coat extract, the extract may be purified using a synthetic adsorbent. Examples of the synthetic adsorbent include porous crosslinked polymer resins of styrene, methacrylate and the like. Examples of the styren resin include DIAION™ HP20 and HP21, and SEPABEADS™ SP825, SP70 and SP700. Examples of the acrylic resin include DIAION™ HP2MGL, and AMBERLITE™ XAD7HP.

The purification using the synthetic adsorbent may be performed by a conventionally known method. For example, the obtained extract is passed through a glass tube filled with a synthetic adsorbent to be adsorbed thereto, impurities and acids are washed out with water, and then an organic solvent or a mixed solvent of an organic solvent and water is used to elute polyphenols adsorbed to the resin.

The black soybean seed coat extract thus prepared may be used as it is as the present composition, or may be subjected to concentration treatment or/and drying treatment from the viewpoint of ingestion or production of food or beverage products. Furthermore, if necessary, the black soybean seed coat extract may be sterilized by a known method such as ultra-high temperature (UHT) sterilization or retort treatment before or after the processing treatment, for the purpose of reducing the number of bacteria in the extract or increasing the shelf life of the extract, as long as the effect of the present invention is not impaired. As used herein, the black soybean seed coat extract may be any of an extraction liquid, a dilution or a concentrate of the extraction liquid, or a dried extract obtained by drying the extraction liquid.

The black soybean seed coat extract prepared as described above contains preferably about 30% w/w or more, for example about 40% w/w or more, for example about 50% w/w to 70% w/w of polyphenols. Among polyphenols, proanthocyanidin, and catechin and epicatechin which are monomers constituting proanthocyanidin are present in a total content of 10% w/w or more, preferably 15% w/w or more, more preferably 20% w/w or more, still more preferably 25% w/w or more, and even still more preferably 30% w/w or more in the black soybean seed coat extract. More preferably, the absorbability of the black soybean seed coat extract into the body when ingested can be enhanced by containing low-polymerization degree (dimer to 9-mer) proanthocyanidins including procyanidin B2, procyanidin C1, cinnamtannin A2 and the like, and catechin and epicatechin which are monomers constituting proanthocyanidin.

[2] Oral Composition and Food or Beverage Composition

The present composition may be in any oral dosage form. As long as the present composition is in an oral dosage (oral ingestion) form, the present composition is applicable to any use [pharmaceuticals, quasi-pharmaceutical products, food or beverage products (including foods with health claims, such as foods for specified health use, foods with functional claims, and foods with nutrient function claims, and supplements)]. The present composition is preferably a food or beverage product, and more preferably a food for specified health use or a food with functional claim that can claim its action or effect. The present composition may be also applied to feed or pet foods for animals other than humans (including livestock, poultry, and pets). The present composition may also be an additive to be added to pharmaceuticals, quasi-pharmaceutical products, food or beverage products, feed, or pet foods.

Specific examples of the oral dosage form include a liquid preparation (including an extract form and a syrup) and a jelly preparation which are prepared from the extract prepared by the above-described extraction method; powder, a fine granule, and a granule which are obtained by formulating the extract into a powder form or a granule form by a conventional method; a capsule (hard capsule or soft capsule) which is filled with the liquid, powder or granule; and a tablet which is formulated by compressing the powder or granule into a tablet form (solid preparation).

The present composition can also be prepared into various dosage forms (oral dosage forms) by combining the black soybean seed coat extract with a known edible carrier, excipient or the like that is pharmaceutically acceptable or acceptable as foods or feed.

When the present composition is prepared in the form of a liquid preparation, a wide variety of carriers conventionally known in the art can be used. Suitable examples of such carriers for producing a liquid preparation and a syrup include water, ethanol, sucrose, converted sugar, glucose, maltose, and reduced starch syrup.

When the present composition is prepared in the form of a solid preparation, for example in the case of a tablet, a wide variety of carriers conventionally known in the art can be used. Examples of such carriers include excipients such as lactose, sucrose, sodium chloride, glucose, urea, starch, calcium carbonate, kaolin, silicic acid and the like; binders such as water, ethanol, propanol, single syrup, glucose solution, starch solution, gelatin solution, carboxymethyl cellulose, shellac, methyl cellulose, potassium phosphate, polyvinylpyrrolidone, crystalline cellulose, hydroxypropyl cellulose, hypromellose, sodium alginate and the like; disintegrants such as dry starch, agar powder, laminaran powder, sodium hydrogen carbonate, polyoxyethylene sorbitan fatty acid esters, sodium lauryl sulfate, stearic acid monoglyceride, starch, crospovidone, povidone, low substituted hydroxypropyl cellulose and the like; disintegration inhibitors such as stearin, cocoa butter, hydrogenated oil and the like; absorption promotors such as quaternary ammonium salts, sodium lauryl sulfate and the like; moisturizers such as glycerin and the like; adsorbents such as starch, lactose, kaolin, bentonite, colloidal silicic acid and the like; and lubricants such as purified talc, stearate, boric acid powder, polyethylene glycol and the like. Furthermore, as necessary, the tablet may be a tablet with an ordinary coating, for example, a sugar-coated tablet, a gelatin-coated tablet, an enteric coated tablet, or a film-coated tablet, or a double layer tablet, or a multilayer tablet. In addition, a capsule can be prepared by filling the composition containing the active ingredient into a conventionally known capsule made of gelatin, pullulan, starch, gum arabic, hydroxypropyl methylcellulose (HPMC) or the like as a raw material.

When the present composition is prepared in the form of a pill, a wide variety of carriers conventionally known in the art can be used. Examples of such carriers include excipients such as glucose, lactose, starch, cocoa butter, hardened vegetable oil, kaolin, talc and the like; binders such as gum arabic powder, tragacanth powder, gelatin, ethanol and the like; and disintegrants such as laminaran, agar and the like.

In addition to the above-mentioned carriers, as an additive, for example, a surfactant, an absorption promotor, an adsorbent, a filler, an antiseptic, a stabilizer, an emulsifier, a solubilizer, and the like can be appropriately selected and used according to the form of the preparation.

All of these forms can be prepared using a conventional method in the art. For example, in the case of a tablet, the active ingredient and an excipient or the like necessary for obtaining a tablet can be mixed well and dispersed, and then compressed into a tablet. In the case of a powder preparation, the active ingredient and an excipient or the like necessary for obtaining a powder preparation can be mixed and then powderized by a suitable method.

In addition to the above-mentioned forms, the present composition may be in the form of an ordinary food or beverage product. The food or beverage product can be produced by adding the above-described black soybean seed coat extract or an additive containing the black soybean seed coat extract as described later to various food or beverage products. The food or beverage product is not particularly limited as long as it is in an orally ingestible form such as a solution, a suspension, an emulsion, a jelly (gel), a sol, a powder, or a solid molded product. Specific examples of the food or beverage product include instant foods, such as instant noodles, boil-in-the-bag foods, canned foods, microwave meals, instant soups or miso-soups, freeze-dried foods and the like; beverages, such as soft drinks, fruit juices, vegetable beverages, soy milk beverages, coffee beverages, tea beverages, powdered drinks, concentrated beverages, energy drinks, alcoholic beverages and the like; flour products, such as bread, pasta, noodles, pancake mix, seasoned flour mix for fried chicken, bread crumbs and the like; confectionery, such as candies, caramels, chewing gums, chocolates, cookies, biscuits, cakes, pies, snacks, crackers, Japanese confectionery, dessert confectionery and the like; condiments, such as sauces, tomato processed seasonings, flavor seasonings, cooking mix, dip sauces, dressings, soup sauces, curry powder, stew mix and the like; fat and oil, such as processed fat and oil, butter, margarine, mayonnaise and the like; dairy products, such as milk beverages, yogurts, cheeses, fermented milks, lactic acid beverages, ice creams, creams and the like; egg processed products, such as pudding, mayonnaise and the like; processed marine products, such as fish meat hams and sausages, fish paste products and the like; livestock processed products, such as meat hams and sausages and the like; agricultural processed products, such as agricultural canned products, jams, marmalades, pickled products, boiled beans, cereals and the like; frozen foods, and nutritional foods. Since the polyphenols derived from the black soybean seed coat extract have high stability under an acidic condition, it is preferable that the present composition is in the form of an acidic food from the viewpoint of suppressing precipitation or color degradation.

In addition, the present composition may be in the form of ordinary feed or pet food. Such feed and pet food can also be produced by adding the black soybean seed coat extract to various feed or pet foods.

The content of the black soybean seed coat extract in the present composition may be appropriately determined up to a ceiling of 100% by mass depending on the form, the use (pharmaceuticals, foods, feed, pet food, etc.) and the like as described above. The dose (ingestion amount) of the present composition may be appropriately varied depending on a human or the kind of an animal, the sex, age, or condition of a subject, or the degree of a symptom. For example, the daily dose (ingestion amount) per an adult human (body weight: 50 kg) can be usually about 10 to 500 mg, for example about 25 to 400 mg, preferably about 50 to 300 mg in terms of the amount of the black soybean seed coat extract (dry weight) contained in the present composition. The present composition is usually orally administered (ingested) once a day or in 2 to 3 divided doses per day. The ingestion timing is not particularly limited, and for example, it may be one or more of the timing of breakfast, lunch or dinner. The present composition may be ingested together with a meal or within 30 minutes before or after a meal.

The present composition exerts an effect on a subject, for example, after the subject was subjected to a mental fatigue load. Examples of the "mental fatigue" include fatigue caused by intellectual labor, mental activities or tension, and fatigue caused by subjective stress such as personal relationships, family relationships and work troubles, as well as jitters caused not only by psychological activities such as complicated calculation, memory or thought but also by simple repeated work or working under patience, tension or time pressure. Thus, the subject that the present composition is administered to is not particularly limited as long as the subject has a subjective symptom of autonomic nervous system imbalance due to fatigue or stress or has a subjective symptom of decreased cognitive function. Examples of the subject include people who engage in visual display terminal (VDT) work or desk work similar thereto, people who have subjective symptoms of decreased brain function such as chronic fatigue syndrome, depression, chronic fatigue, sense of drag, decline in motivation, decline in concentration, memory decline, or impaired judgment, and people who need or demand prevention of the above-mentioned symptoms.

The autonomic nervous system modulatory function or the cognitive function can be improved by orally taking (administering or ingesting) the present composition, or a decrease in the autonomic nervous system modulatory function or the cognitive function can be suppressed by orally taking (administering or ingesting) the present composition. For example, when the present composition is taken (administered, or ingested), the function improvement effect can be evaluated or determined by using a pulse-analyzer device for the autonomic nervous modulatory function or using cognitive function measurement (CogEvo Ri) composed of 8 tasks which was developed under the supervision of RIKEN for the cognitive function. Regarding the autonomic nervous system modulatory function, a low frequency region (0.04 to 0.15 Hz) power value (LF) obtained by frequency analysis using a pulse-analyzer device reflects both the sympathetic nerve activity and the parasympathetic nerve activity, and a high frequency region (0.15 to 0.40 Hz) power value (HF) is regarded as an index of the parasympathetic nerve function.

[3] Method for Using Black Soybean Seed Coat Extract

The present invention also provides a method for using the black soybean seed coat extract. An example of the use method is a method of using the black soybean seed coat extract for imparting the ability to improve an autonomic nervous system modulatory function, the ability to suppress a decrease of a cognitive function, or the ability to improve a cognitive function to an oral composition or a food or beverage composition.

The use method is based on the ability to improve an autonomic nervous system modulatory function, the ability to suppress a decrease of an autonomic nervous system modulatory function, the ability to suppress a decrease of a cognitive function, or the ability to improve a cognitive function which the black soybean seed coat extract possesses, and may be a method of using the black soybean seed coat extract for producing an oral composition or a food or beverage composition. Instead of the black soybean seed coat extract, the above-described present composition containing the black soybean seed coat extract as an active ingredient can also be used.

The oral composition or food or beverage composition may be any composition to be orally administered to a human or any composition to be ingested by a human, and specific examples thereof include oral pharmaceuticals, oral quasi-pharmaceutical products, and food or beverage products. Food or beverage products are preferred. When a non-human animal is a subject, feed or pet foods can be used as the oral composition.

The kind of black soybean used as a raw material of the black soybean seed coat extract used in the method of the present invention, a method for obtaining black soybean seed coats, and a method for preparing the black soybean seed coat extract, particularly a black soybean seed coat acidic extract which is a preferred embodiment of the extract are as described in above section [1], which can be incorporated in this section. The amount of the black soybean seed coat extract contained in the oral composition or the food or beverage composition is not particularly limited as long as it is an amount capable of imparting the ability to improve an autonomic nervous system modulatory function, the ability to suppress a decrease of an autonomic nervous system modulatory function, the ability to improve a cognitive function, or the ability to suppress a decrease of a cognitive function to the oral composition or the food or beverage composition. The impartation can be evaluated and confirmed by, for example, a pulse-analyzer device and cognitive function measurement [CogEvo Ri: orientation function (time management), planning ability (route 99)] in a case where an oral composition or a food or beverage composition containing the black soybean seed coat extract (intended composition) is continuously ingested by a subject and in a case where an oral composition or a food or beverage composition not containing the black soybean seed coat extract (comparative composition) is continuously ingested by a subject.

The present invention also provides a method for modulating an autonomic nervous system, the method comprising administering the black soybean seed coat extract to a subject. Furthermore, the present invention provides a method for improving a cognitive function, the method comprising administering the black soybean seed coat extract to a subject. Examples of the subject include human and non-human animals (for example, livestock, poultry, pets, and the like). The black soybean seed coat extract may be in the form of the present composition. The dose of the black soybean seed coat extract can be appropriately determined depending on the kind, sex, age, or condition of a subject, or the degree of a symptom. For example, the daily dose per an adult human (body weight: 50 kg) of the black soybean seed coat extract can be usually about 10 to 500 mg, for example about 25 to 400 mg, preferably about 50 to 300 mg. The black soybean seed coat extract is usually orally administered once a day or in 2 to 3 divided doses per day.

EXAMPLES

Hereinafter, the present invention will be explained in more detail with reference to experimental examples which the present invention is not limited to.

[Example 1] Improvement of Autonomic Nervous System Modulatory Function or Cognitive Function by Black Soybean Seed Coat Extract First, methods for preparing a black soybean seed coat extract and a test food, and then a method for testing the improvement of an autonomic nervous modulatory function and a cognitive function and results thereof are described.

[Black Soybean Seed Coat Extract]

A black soybean seed coat extract (an extract with acidic hot water) was prepared by the following method.

(1) One kilogram of black soybean seed coats (raw) were immersed in 30 L of dilute sulfuric acid (0.3% w/v) as an extraction solvent, and extracted for 20 minutes while being stirred and heated to 55 to 60° C.

(2) After extraction, a liquid fraction was separated from the black soybean seed coats by solid-liquid separation, and then collected.

(3) The collected liquid was centrifuged to remove suspended solids that could not be removed by solid-liquid separation.

(4) An extract thus obtained was applied to a column filled with synthetic adsorption resin (SEPABEADS™ SP700: manufactured by Mitsubishi Chemical Corporation), and adsorbed to the resin.

(5) In order to wash away the sulfuric acid remaining in the column, water was passed through the column to wash the resin.

(6) An aqueous solution containing 59% by volume of alcohol was passed through the column to elute polyphenols adsorbed to the resin.

(7) An eluate (alcohol solution) was collected and then evaporated by heating under reduced pressure to be concentrated.

(8) To a concentrate, dextrin was added as an excipient.

(9) The concentrate was sterilized by heating.

(10) After heat sterilization, the concentrate was spray-dried to obtain a black soybean seed coat extract (85 g, polyphenol content: 61.1%).

[Component Composition of Black Soybean Seed Coat Extract]

The component composition of the black soybean seed coat extract (acidic hot water extract) obtained as described above was analyzed by a method as described below. Results are shown in Table 1.

(1) Analysis of Total Polyphenol

The black soybean seed coat extract was adjusted to a concentration of 7.5 mg/100 ml with 70% ethanol to obtain a sample solution. To 1 ml of the sample solution, 5 ml of a Folin Ciocalteu solution was added and reacted. After 4 ml of a 0.7 M aqueous sodium carbonate solution was added, a mixture was stirred, and allowed to stand still at 30° C. for 60 minutes. Then, an absorbance at 765 nm was measured with a spectrophotometer. At the same time, a calibration curve of catechin ("(+)-catechin hydrate" C1251-5G, manufactured by SIGMA) was prepared, and a total amount of polyphenol was calculated as a catechin equivalent.

(2) Analysis of Total Flavan-3-Ol

The black soybean seed coat extract was adjusted to a concentration of 12.5 mg/100 ml with 50% ethanol to obtain a sample solution. To 1 ml of the sample solution, 3 ml of a 4% vanillin solution was added and stirred. After 1.5 ml of concentrated hydrochloric acid was added and stirred, a mixture was allowed to stand still at 30° C. for 20 minutes. Then, an absorbance at 500 nm was measured with a spectrophotometer. As a control, 100% methanol was added instead of the 4% vanillin solution. In the spectrophotometer measurement, the absorbance of the sample was calculated by the following equation.

Absorbance of sample=$A-B-C$ wherein, A is the absorbance measured in the test sample, B is the absorbance measured in the control, and C is the absorbance measured in a blank test. At the same time, a calibration curve of catechin ("(+)-catechin hydrate" C1251-5G, manufactured by SIGMA) was prepared, and a total amount of flavan-3-ol was calculated as a catechin equivalent.

(3) Analysis of Catechin, Epicatechin, Procyanidin B2, Procyanidin C1, and Cinnamtannin A2

The black soybean seed coat extract was adjusted to a concentration of 0.1 mg/ml with 50% ethanol to prepare a sample solution. The sample solution was subjected to HPLC under analysis conditions as described below. A 0.1% formic acid solution was used as mobile phase A, and acetonitrile was used as mobile phase B. Elution was performed under concentration gradients and conditions as described below. At the same time, each standard solution of catechin, epicatechin, procyanidin B2, procyanidin C1, or cinnamtannin A2 was subjected to HPLC, and calibration were prepared for quantification.

Concentration gradient: 0 to 45 min/B: 5 to 15%, 45 to 50 min/B: 15 to 80%, 50 to 53 min/B: 80%, 53 to 70 min/B: 5%, flow rate: 0.7 mL/min, injection amount: 10 µL, column oven temperature: 40° C., fluorescence: excitation wavelength 276 nm, light emission: 316 nm, Cadenza CL-C18 column (φ 250 mm×4.6 mm, 3 µm, Imtakt), guard column (Cadenza CL-C18, φ 5 mm×2 mm, 3 µm, Imtakt)

(4) Analysis of Cyanidin 3-Glucoside

The black soybean seed coat extract was adjusted to a concentration of 0.1 mg/ml with 1% hydrochloric acid-methanol (1:37, v/v) to prepare a sample solution. The sample solution was subjected to HPLC under analysis conditions as described below. A solution of a formic acid:water (3:97, v/v) was used as mobile phase A, and a solution of formic acid:acetonitrile:water (3:30:67, v/v) was used as mobile phase B. Elution was performed under concentration gradients and conditions as described below. At the same time, a standard solution of cyanidin 3-glucoside was subjected to HPLC, and a calibration curve was prepared for quantification. Concentration gradient: 0 to 50 min/B: 25 to 50%, 50 to 55 min/B: 50 to 100%, 55 to 60 min/B: 100%, 60 to 70 min/B: 25%, flow rate: 0.6 mL/min, injection amount: 10 µL, column oven temperature: 40° C., UV: measurement wavelength 520 nm, Cadenza CL-C18 column ((250 mm×4.6 mm, 3 µm, Imtakt), guard column (Cadenza CL-C18, φ 5 mm×2 mm, 3 µm, Imtakt)

TABLE 1

| Total Polyphenol | 61.10% |
|---|---|
| Total Flavan-3-ol | 33.20% |
| Catechin | 0.20% |
| Epicatechin | 4.61% |
| Procyanidin B2 | 5.62% |
| Procyanidin C1 | 1.38% |
| Cinnamtannin A2 | 0.46% |
| Cyanidin 3-glucoside | 2.10% |

[Test Food]

A black soybean seed coat extract-containing food (test food) and a control food (placebo) were used and tested. The composition of these foods is shown as below.

Test food: A capsule (210 mg in total) containing 100 mg of the black soybean seed coat extract (polyphenol content: 61.1%) and 110 mg of dextrin Placebo: A capsule containing 250 mg of dextrin The placebo was prepared so as not to have a large difference in heat quantity or the like as compared to the test food. Nutrient composition of each food is shown in Table 2.

TABLE 2

Test food composition [per daily ingestion amount (one capsule)]

| Heat quantity/<br>component composition | Test food | Placebo |
|---|---|---|
| Black soybean seed coat extract (mg) | 100 | 0 |
| Heat quantity (kcal) | 1 | 1 |
| Protein (g) | 0.1 | 0.1 |
| Fat (g) | 0.01 | 0.01 |
| Carbohydrate (g) | 0.2 | 0.2 |
| Sodium (mg) | 0.02 | 0.01 |

[Test Method]

(Implementation System)

This study was conducted in accordance with the spirit of the Declaration of Helsinki (2013)-amended by Tokyo, Venice, Hong Kong, Somerset West, and Edinburgh, annotation added by Washington, and Tokyo, amended by Seoul, and amended by Fortaleza, always in consideration of the protection of human rights of test subjects, under the control of physicians with approval of Institutional Review Board (IRB) of medical corporation KOSEIKAI, FUKUDA CLINIC. The implementation followed the "Ethical Guidelines for Medical and Health Research Involving Human Subjects (issued on Dec. 22, 2014)".

(Subject)

Subjects were a total of 24 healthy men and women (12 men and women each) 20 years of age and older and younger than 65 years of age, determined by screening from 77 subject candidates who were judged appropriate to participate in the present test by an investigator. For participating in the present study, the subjects received an explanation of the present test in advance, and understood the contents of the test and approved the test purpose, and written consent was obtained from the subjects. The healthy subjects were basically not people who has subjective symptoms of a decrease in the cognitive function. Further, subjects with soybean allergy, subjects who regularly take medicines, subjects with serious cardio-vascular disorder, liver function disorder, renal function disorder, respiratory disorder, endocrine disorder or metabolic disorder or having a medical history of the above-mentioned disorders, subjects with chronic fatigue syndrome (CFS), subjects deemed to have severe fatigue such as idiopathic chronic fatigue by the investigator, subjects who regularly take pharmaceuticals or quasi-pharmaceutical products having effect-efficacy of recovering from fatigue or supplying nutrients for physical fatigue, subjects who regularly take foods with functional claims related to fatigue feeling, female subjects who are pregnant or lactating, female subjects intending to become pregnant, subjects having a blood sample (such as blood donation) of 200 mL or more taken within 1 month, or 400 mL or more taken within 3 months before the start of the present study, subjects who participated in other clinical studies within the past 3 months, subjects currently participating in other clinical studies, and subjects deemed unsuitable by the investigator were excluded.

(Ingestion of Test Food)

One capsule per day of the test food or placebo was ingested after dinner continuously for 4 weeks. During the study period, the subjects were prohibited from ingesting pharmaceuticals or quasi-pharmaceutical products having effect-efficacy of recovering from fatigue or supplying nutrients for physical fatigue, and food or beverage products that might have anti-fatigue effect such as foods with functional claims related to fatigue feeling or healthy foods containing a high amount of antioxidants.

(Test Method)

The study was designed to be a randomized double-blinded placebo-controlled crossover comparison trial. The study design is shown in FIG. 1.

Mental work was loaded on the subjects on a test day at the start of ingestion and a test day after ingestion for 4 weeks in the first study period, and on a test day at the start of ingestion and a test day after ingestion for 4 weeks in the second study period for crossover after a 4-weeks washout period. The subjects were prohibited from drinking alcohol and coffee on the test days and days before the test days. During the study periods, though the subjects were not particularly limited in physical activities, the subjects maintained their regular exercise habits (frequency, type of exercise, etc.) as much as possible, and were prohibited from suddenly changing their states, for example, suddenly training hard, running a full marathon, or suddenly stopping an exercise that had been regularly performed. The subjects for the present study must not use pharmaceuticals without the permission of the investigator until the end of the study.

(Mental Work Load)

The subjects performed 2 sets (2 hours) of tasks in which one set was a total of 1 hour composed of a 30-min 2-back task and a 30-min advanced trail making test (ATMT) (also known as the ABC task), as a mental fatigue load caused by visual display terminal (VDT) work. [The instructions of the 2-back task and ATMT (ABC task) were performed on days before the test days of the present study.]

(1) 2-Back Task

The 2-back task is a short-term memory task performed using a computer screen displaying a random alphabet every three seconds, which comprises clicking the right mouse button when the currently displayed alphabet was the same as the alphabet displayed two characters ago, and clicking the left mouse button when the currently displayed alphabet was different from the alphabet displayed two characters ago.

(2) ATMT (ABC Task)

ATMT is a visual search task which comprises quickly clicking on 25 numbers from 1 to 25 randomly displayed on a computer screen in the order from 1 to 25. Three types of tasks A, B, and C were sequentially performed. In task A, the arrangement of numbers from 1 to 25 is not changed. In task B, the arrangement of numbers from 1 to 25 is not changed, clicked numbers disappear, and new numbers from 26 are added. Task C is the same as task B except that the arrangement of numbers from 1 to 25 is changed.

(Test Items)

(1) Evaluation of Autonomic Nervous Function

The autonomic nervous function was evaluated on the test day at the start of ingestion and on the test day after ingestion for 4 weeks, five times on each test day, i.e. before work load, after 1-hour work load, after 2-hours work load, after a 1-hour recovery time, and after a 2-hours recovery time, by measuring an acceleration plethysmogram using ARTETT CDN (U-MEDICA INC.) and performing frequency analysis of a-a intervals using a maximum entropy method (MEM) for main analysis and a fast Fourier transform (FFT) for sub-analysis. Specifically, a power spectrum was integrated from 0.04 Hz to 0.15 Hz to obtain a power value of LF (Low Frequency, Low-Frequency Component), and integrated from 0.15 Hz to 0.4 Hz to obtain a power value of HF (High Frequency, High-Frequency Component). Then, LF % and HF %, a percentage (% value) of the obtained LF or HF in total power (total frequency range integrated value), were calculated. As an index value of autonomic nervous system activity, LF/HF (low frequency component/high frequency component), which is indicative of a sympathetic nerve activity, was calculated.

(2) Visual Analogue Scale (VAS) Test

A VAS test was performed on the test day at the start of ingestion and on the test day after ingestion for 4 weeks, five times on each test day, i.e. before work load, after 1-hour work load, after 2-hours work load, after a 1-hour recovery time, and after a 2-hours recovery time. Question items were fatigue feeling, drowsiness, eyestrain, and shoulder stiffness.

VAS is recommended by the Japanese Society of Fatigue Science as a method for evaluating fatigue feeling. For scoring VAS self-evaluation, a horizontal straight line of 10.0 cm length was used. A level of the subject's sense for each question item was marked on a line segment between both ends, indicating the most negative evaluation (feeling no sense) at the left end and indicating the most positive evaluate (feeling a sense) at the right end. For evaluation results, a distance of a point marked by each subject from the left end was measured and digitized. The most negative evaluation (left end) was represented as 0 point, and the most positive evaluation (right end) was represented as 10.0 points.

(3) Jikaku-Sho Shirabe

Jikaku-sho shirabe (subjective symptom questionnaire by Working Group for Occupational Fatigue) was performed on the test day at the start of ingestion and on the test day after ingestion for 4 weeks, three times on each test day, i.e. before work load, after 2-hours work load, and after a 2-hours recovery time.

Jikaku-sho shirabe is recommended by the Working Group for Occupational Fatigue as a method for evaluating fatigue feeling which comprises grasping temporal change under a fatigue situation associated with work. The Jikaku-sho shirabe is composed of 25 questions which are categorized into five groups, and a total score is determined for each groups to evaluate the fatigue situation for each group. The five groups include Group 1: feeling of drowsiness, Group 2: feeling of instability, Group 3: feeling of uneasiness, Group 4: feeling of local pain or dullness, and Group 5: feeling of eyestrain.

(4) Cognitive Function Test

A cognitive function test was performed using CogEvo Ri (TOTAL BRAIN CARE, CO., LTD.) on the test day at the start of ingestion and on the test day after ingestion for 4 weeks, three times on each test day, i.e. before work load, after 2-hours work load, and after a 2-hours recovery time. CogEvo Ri has been used in clinical studies in various medical and living fields related to cognitive function mainly in the elderly field, and has shown validity of cognitive function evaluation in clinical trials. A task related to cognitive function was performed using a tablet terminal, and the cognitive function was evaluated by scoring.

(5) Statistical Processing

Test data were counted and statistically analyzed for each item. SPSS Ver.22.0 (IBM Japan, Ltd.) was used as statistical processing software. For comparison between the test conditions, a paired t-test was performed. A significance level was 5% by a two-sided test, and 10% was regarded as having a tendency.

[Results]
(Subject)

Figure 2:
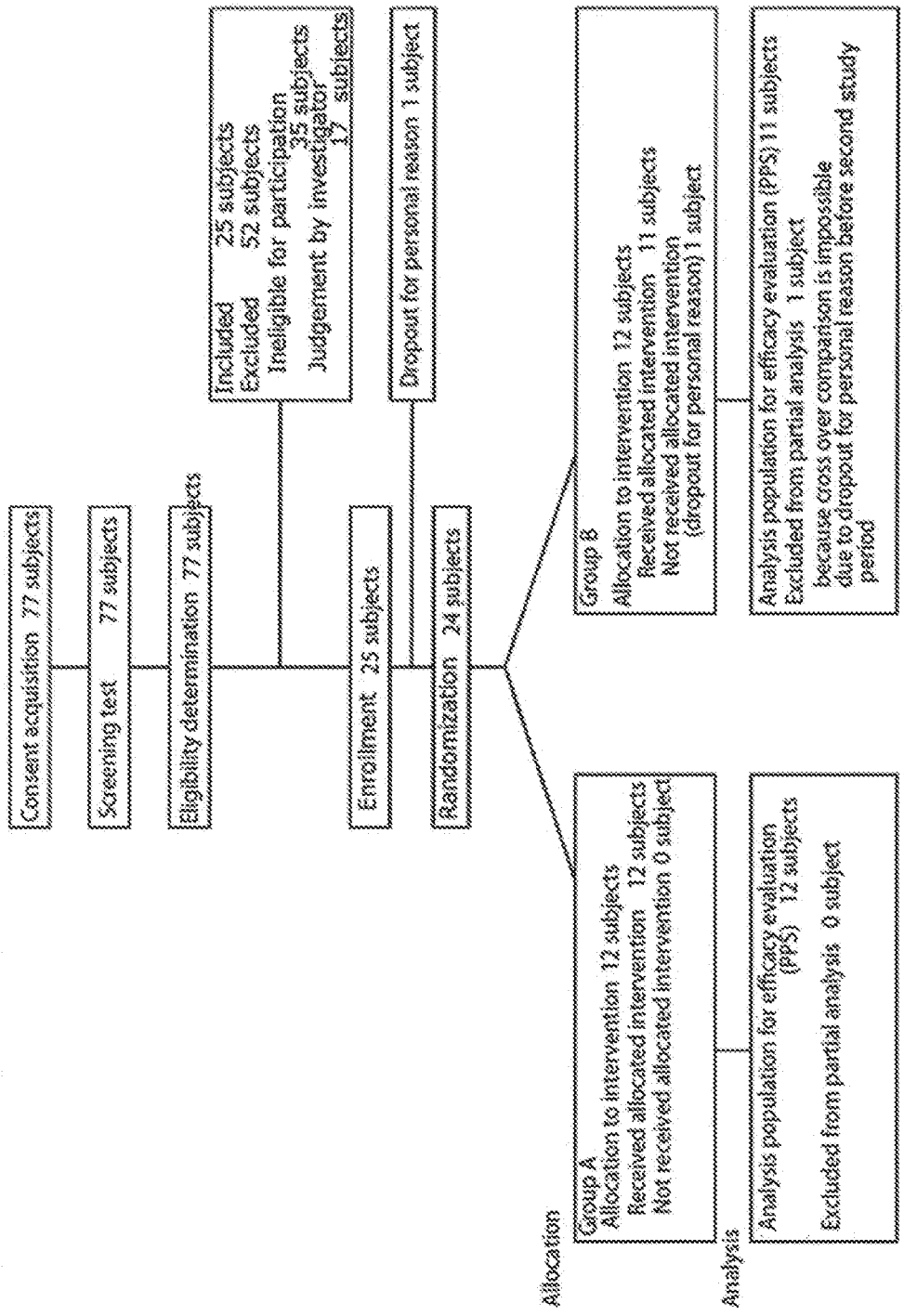
FIG. 2 is a diagram showing a flowchart of subjects.

Twenty-four subjects were randomly allocated to 2 groups (test food group: 12 subjects, placebo group: 12 subjects) so as to have the same male/female ratio, and a crossover test was performed. During the study periods, one subject dropped out of the second study period, and crossover comparison could not be performed. Thus the subject was excluded. A flowchart of subjects is shown in FIG. 2.

(1) Evaluation of Autonomic Nervous System Function

Regarding differences in changes from values before work load between before and after the start of ingestion in the autonomic nervous system function evaluation, in the test food group, LF %-MEM, LF %-FFT, and LF/HF-MEM were significantly decreased after a 1-hour recovery time, and HF-MEM and HF-FFT were significantly increased after 2-hours work load and after a 1-hour recovery time, as compared with the placebo group (Table 3).

On the other hand, before work load, in the test food group, the measured value of HF-MEM was significantly low and the measured value of LF/HF-FFT was significantly high as compared with the placebo group (Table 4). It is known that LF mainly reflects sympathetic nerve activity, HF reflects parasympathetic nerve activity, and sympathetic nerve activity is dominant in a fatigue state. The test food group showed a parasympathetic nerve activity dominant state suited to recovery after work load and a sympathetic nerve dominant state suited to activity before work load.

TABLE 3

Autonomic nervous system function evaluation (a-a interval frequency-domain analysis of acceleration plethysmogram) Difference in change from value before work load between before and after the start of ingestion

| | | After 1-hour work load Test food: n = 23 Placebo: n = 23 | After 2-hours work load Test food: n = 23 Placebo: n = 23 | After 1-hour recovery Test food: n = 23 Placebo: n = 23 | After 2-hours recovery Test food: n = 23 Placebo: n = 23 |
|---|---|---|---|---|---|
| LF-MEM ($msec^2$) | Test food | −38.2 ± 600.9 | −155.5 ± 545.1 | 3.6 ± 826.3 | −48.5 ± 368.6 |
| | Placebo | 73.5 ± 532.2 | 97.5 ± 600.2 | 147.8 ± 636.2 | −6.3 ± 792.4 |
| LF %-MEM (%) | Test food | −9.1 ± 20.5 | −7.8 ± 28.0 | −10.7 ± 33.6 ]** | −3.3 ± 32.7 |
| | Placebo | −2.6 ± 24.3 | 4.7 ± 22.3 | 11.7 ± 23.2 | 7.1 ± 29.2 |
| LF-FFT ($msec^2$) | Test food | 6.9 ± 659.8 | −127.3 ± 479.7 | 65.2 ± 709.1 | −29.9 ± 344.5 |
| | Placebo | 99.7 ± 575.4 | 54.9 ± 660.2 | 140.2 ± 640.6 | −15.7 ± 850.1 |
| LF %-FFT (%) | Test food | −3.6 ± 15.0 | −5.6 ± 23.7 | −7.1 ± 23.2 ]* | −3.0 ± 29.5 |
| | Placebo | −1.5 ± 24.5 | 3.7 ± 21.2 | 10.4 ± 23.0 | 7.6 ± 31.9 |
| HF-MEM ($msec^2$) | Test food | 3.8 ± 277.8 | 51.8 ± 260.4 ]* | 204.2 ± 663.2 ]* | −61.6 ± 373.7 |
| | Placebo | 35.7 ± 835.5 | −227.4 ± 450.7 | −289.7 ± 630.3 | −317.6 ± 508.1 |
| HF %-MEM (%) | Test food | 0.6 ± 17.9 | 2.7 ± 27.9 | 2.4 ± 22.5 | −1.1 ± 24.5 |
| | Placebo | −3.3 ± 20.4 | −7.2 ± 26.4 | −11.3 ± 24.2 | −9.2 ± 21.4 |
| HF-FFT ($msec^2$) | Test food | −21.6 ± 263.1 | 23.5 ± 238.2 ]* | 166.1 ± 640.4 ]* | −100.1 ± 389.9 |
| | Placebo | 39.4 ± 837.6 | −233.0 ± 458.3 | −288.5 ± 631.2 | −312.0 ± 477.2 |
| HF %-FFT (%) | Test food | −1.4 ± 15.9 | 1.2 ± 24.2 | 0.5 ± 20.8 | −3.5 ± 26.5 |
| | Placebo | −3.3 ± 20.5 | −7.5 ± 26.3 | −10.8 ± 23.0 | −9.1 ± 20.7 |
| LF/HF-MEM | Test food | −0.043 ± 3.228 | −0.270 ± 3.570 | −0.727 ± 3.966 ]* | −0.342 ± 3.070 |
| | Placebo | −0.127 ± 2.631 | 0.843 ± 3.306 | 1.194 ± 3.107 | 0.982 ± 3.262 |
| LF/HF-FFT | Test food | 0.599 ± 2.064 | 0.166 ± 2.153 | −0.016 ± 1.993 | 0.214 ± 2.243 |
| | Placebo | 0.016 ± 2.354 | 0.792 ± 3.030 | 1.066 ± 2.588 | 1.038 ± 2.788 |

Average value ± standard deviation
Comparison between groups (paired t-test):
**p < 0.01,
*p < 0.05

TABLE 4

Autonomic nervous system function evaluation (a-a interval frequency-domain analysis of acceleration plethysmogram) Measured value

| | | Test day at start of ingestion Before work load Test food: n = 23 Placebo: n = 23 | Test day after 4-weeks ingestion Before work load Test food: n = 23 Placebo: n = 23 |
|---|---|---|---|
| LF-MEM ($msec^2$) | Test food | 278.8 ± 279.5 | 282.5 ± 239.4 |
| | Placebo | 360.0 ± 491.2 | 300.4 ± 320.7 |
| LF %-MEM (%) | Test food | 21.2 ± 12.3 | 28.1 ± 19.0 |
| | Placebo | 23.5 ± 18.5 | 19.2 ± 11.3 |
| LF-FFT ($msec^2$) | Test food | 308.8 ± 292.0 | 285.4 ± 228.5 |
| | Placebo | 396.7 ± 470.3 | 349.8 ± 355.3 |
| LF %-FFT (%) | Test food | 24.6 ± 11.6 | 28.6 ± 13.8 |
| | Placebo | 26.7 ± 16.7 | 22.6 ± 12.1 |
| HF-MEM ($msec^2$) | Test food | 316.7 ± 312.6 | 235.5 ± 197.2 ]* |
| | Placebo | 286.1 ± 242.2 | 510.8 ± 599.2 |
| HF %-MEM (%) | Test food | 26.4 ± 16.3 | 26.2 ± 17.6 |
| | Placebo | 23.4 ± 13.7 | 30.7 ± 17.7 |
| HF-FFT ($msec^2$) | Test food | 325.8 ± 315.9 | 270.2 ± 213.9 |
| | Placebo | 292.9 ± 246.4 | 524.2 ± 606.9 |
| HF %-FFT (%) | Test food | 27.8 ± 16.7 | 29.4 ± 17.9 |
| | Placebo | 24.2 ± 13.9 | 31.9 ± 17.5 |
| LF/HF-MEM | Test food | 1.467 ± 1.787 | 1.933 ± 2.535 |
| | Placebo | 1.644 ± 2.592 | 1.028 ± 1.350 |
| LF/HF-FFT | Test food | 1.599 ± 1.721 | 1.487 ± 1.195 ]* |
| | Placebo | 1.712 ± 2.081 | 1.078 ± 1.218 |

Average value ± standard deviation
Comparison between groups (paired t-test):
* p < 0.05

(2) Visual Analogue Scale (VAS) Test
(2-1) Fatigue Feeling

Regarding the measured values, the test food group showed significantly low values of the fatigue feeling before work load, after 1-hour work load, and after 2-hours work load on the test day after ingestion for 4 weeks, as compared with the placebo group. Since a significantly low value was observed before work load, it was found that the fatigue feeling caused by daily life was alleviated by ingestion of the test food for 4 weeks. Since significantly low values were observed after 1-hour work load and after 2-hours work load, it was found that the alleviation of the fatigue feeling was continued even when the mental work was loaded. Results of measured VAS values are shown in Table 5. Numerical values are the average value and its standard error.

(2-2) Drowsiness

Regarding the measured values, the test food group showed significantly low values of drowsiness before work load and after 2-hours work load on the test day after ingestion for 4 weeks, as compared with the placebo group. Since drowsiness is probably induced by fatigue, such a change in drowsiness is probably associated with the fatigue feeling-alleviating effect of the test food containing the black soybean seed coat extract. Results of measured VAS values are shown in Table 5. Numerical values are the average value and its standard error.

(2-3) Shoulder Stiffness

Regarding the measured values, the test food group showed a tendency of a low value of shoulder stiffness after 1-hour work load on the test day after ingestion for 4 weeks, as compared with the placebo group. Thus it is suggested that shoulder stiffness symptoms caused by mental work load were alleviated. Results of measured VAS values are shown in Table 5. Numerical values are the average value and its standard error.

(2-4) Eyestrain

Regarding a change in VAS from the test day at the start of ingestion, the test food group showed a significant decrease of eyestrain on the test day after ingestion for 4 weeks, suggesting that the test food containing the black soybean seed coat extract had an alleviating effect on eyestrain. Results of a change in VAS from the test day at the start of ingestion are shown in Table 6. Numerical values are the average value and its standard error.

(3) Jikaku-Sho Shirabe
(3-1) Feeling of Uneasiness

Regarding the measured values, the test food group showed significantly low values of group 3 (feeling of uneasiness) before work load and after 2-hours work load on the test day after ingestion for 4 weeks, as compared with the placebo group. Thus it was found that the test food containing the black soybean seed coat extract had an alleviating effect on the feeling of uneasiness associated with fatigue. Since feeling of uneasiness is a sensation often observed with fatigue, such a result shows the mental fatigue-alleviating effect of the black soybean seed coat extract. Results of measured values of Jikaku-sho shirabe are shown in Table 7. Numerical values are the average value and its standard error.

(3-2) Drowsiness

Regarding the measured values, the test food group showed a tendency of decrease in group 1 (feeling of drowsiness) before work load on the test day after ingestion for 4 weeks and a significantly low value of group 1 (feeling of drowsiness) after 2-hours work load on the test day after ingestion for 4 weeks, as compared with the placebo group. Such results support the alleviation of drowsiness found by VAS. Results of measured values of subjective symptom examination are shown in Table 7. Numerical values are the average value and its standard error.

TABLE 5

VAS On test day after 4-weeks ingestion, Measured value

|  |  | On test day after 4-weeks ingestion before work load Test food: n = 23 Placebo: n = 23 | On test day after 4-weeks ingestion after 1-hour work load Test food: n = 23 Placebo: n = 23 | On test day after 4-weeks ingestion after 2-hours work load Test food: n = 23 Placebo: n = 23 | On test day after 4-weeks ingestion after 1-hour recovery Test food: n = 23 Placebo: n = 23 | On test day after 4-weeks ingestion after 2-hours recovery Test food: n = 23 Placebo: n = 23 |
|---|---|---|---|---|---|---|
| Fatigue feeling | Test food | 43.9 ± 17.9  ]* | 62.5 ± 19.4  ]* | 66.3 ± 19.8  ]* | 51.8 ± 22.2 | 48.3 ± 22.2 |
|  | Placebo | 53.9 ± 17.5 | 69.8 ± 12.7 | 73.7 ± 12.1 | 55.5 ± 17.3 | 50.2 ± 22.6 |
| Eyestrain | Test food | 43.9 ± 21.7 | 64.4 ± 21.5 | 68.1 ± 22.1 | 54.5 ± 22.2 | 47.6 ± 24.3 |
|  | Placebo | 48.0 ± 23.8 | 69.9 ± 14.5 | 72.3 ± 19.8 | 53.7 ± 20.8 | 48.0 ± 25.7 |
| Drowsiness | Test food | 48.7 ± 20.7  ]* | 70.2 ± 19.1 | 71.7 ± 19.9 | 54.0 ± 25.0 | 48.1 ± 23.4 |
|  | Placebo | 61.0 ± 22.4 | 74.6 ± 18.3 | 80.0 ± 15.3  ]* | 58.6 ± 20.9 | 51.7 ± 28.7 |
| Shoulder stiffness | Test food | 42.7 ± 26.0 | 54.0 ± 24.2  ]† | 61.2 ± 26.4 | 50.2 ± 24.0 | 46.3 ± 22.1 |
|  | Placebo | 46.9 ± 27.3 | 61.2 ± 22.8 | 65.9 ± 23.8 | 50.6 ± 21.6 | 47.9 ± 29.7 |

Average value ± standard deviation
Comparison between groups (paired t-test): *p < 0.05, †p < 0.1

TABLE 6

VAS Change from test day at start of ingestion

|  |  | On test day after 4-weeks ingestion before work load Test food: n = 23 Placebo: n = 23 |
|---|---|---|
| Fatigue feeling | Test food | −8.0 ± 22.5 |
|  | Placebo | −2.3 ± 18.8 |
| Eyestrain | Test food | −9.3 ± 19.1  ] * |
|  | Placebo | 2.2 ± 13.0 |
| Drowsiness | Test food | −8.7 ± 19.1 |
|  | Placebo | 0.9 ± 22.0 |
| Shoulder stiffness | Test food | −4.6 ± 19.0 |
|  | Placebo | −0.7 ± 23.6 |

Average value ± standard deviation
Comparison between groups (paired t-test):
* p < 0.05,
†p < 0.1

TABLE 7

Jikaku-sho shirabe, On test day after 4-weeks ingestion, Measured value

| | | On test day after 4-weeks ingestion before work load Test food: n = 23 Placebo: n = 23 | On test day after 4-weeks ingestion after 2-hours work load Test food: n = 23 Placebo: n = 23 | On test day after 4-weeks ingestion after 2-hours recovery Test food: n = 23 Placebo: n = 23 |
|---|---|---|---|---|
| Group 1 (feeling of drowsiness) | Test food Placebo | 11.3 ± 4.4 ]† 12.5 ± 4.6 | 15.3 ± 4.8 ]* 16.8 ± 4.8 | 11.7 ± 4.6 12.5 ± 5.3 |
| Group 2 (feeling of instability) | Test food Placebo | 7.7 ± 2.9 8.2 ± 3.1 | 9.3 ± 3.9 10.5 ± 5.3 | 6.9 ± 3.1 7.7 ± 3.5 |
| Group 3 (feeling of uneasiness) | Test food Placebo | 7.3 ± 2.0 ]** 8.7 ± 3.1 | 9.7 ± 3.5 ]** 11.5 ± 4.5 | 7.9 ± 3.1 8.6 ± 3.8 |
| Group 4 (feeling of local pain or dullness) | Test food Placebo | 7.7 ± 2.1 8.3 ± 3.2 | 10.6 ± 3.6 10.8 ± 4.2 | 8.8 ± 2.9 8.4 ± 2.3 |
| Group 5 (feeling of eyestrain) | Test food Placebo | 9.2 ± 3.5 9.7 ± 4.3 | 13.6 ± 4.4 14.3 ± 5.5 | 10.4 ± 3.5 10.4 ± 4.9 |

Average value ± standard deviation
Comparison between groups (Wilcoxon signed rank test):
** $p < 0.01$,
* $p < 0.05$,
† $p < 0.1$ (4) Cognitive Function Test Regarding the measured values, the test food group showed a significantly high score of orientation function/time management after 2-hours work load on the test day after ingestion for 4 weeks (Table 8). The test food group also showed an increased score of planning ability/route 99 after 2-hours work load (Table 8). Thus it was found that the test food group improved a reduction in the cognitive function caused by a mental work load as compared with the placebo group.

TABLE 8

Cognitive function test, On test day after 4-weeks ingestion, Measured value

| | | On test day after 4-weeks ingestion before work load Test food: n = 23 Placebo: n = 23 | On test day after 4-weeks ingestion after 2-hours work load Test food: n = 23 Placebo: n = 23 | On test day after 4-weeks ingestion after 2-hours recovery time Test food: n = 23 Placebo: n = 23 |
|---|---|---|---|---|
| Orientation function Time management Score | Test food Placebo | 314.0 ± 63.1 308.9 ± 51.9 | 304.7 ± 57.4 ]* 277.0 ± 55.7 | 297.1 ± 61.4 316.2 ± 64.6 |
| Planning ability Route 99 Score | Test food Placebo | 117.3 ± 66.7 130.6 ± 59.9 | 158.1 ± 45.7 ]† 142.1 ± 62.0 | 151.0 ± 58.2 150.3 ± 59.0 |

Average value ± standard deviation
Comparison between groups (paired t-test):
* $p < 0.05$,
† $p < 0.1$ These results show that the autonomic nervous modulatory function and the cognitive function are improved by orally ingesting the test food (black soybean seed coat extract). At least regarding a dose range of the black soybean seed coat extract (acidic hot water extract) studied herein, the desired effect of the present invention was produced by 100 mg or more (dry weight) of the black soybean seed coat extract (acidic hot water extract).

Formulation examples of the black soybean seed coat extract are described below.

Formulation Example 1: Soft Capsule

A soft capsule was prepared according to a conventional method using raw materials as cited below. As a black soybean seed coat extract, the black soybean seed coat extract prepared according to the method of Example 1 was used.

Vegetable oil and fat: 158.6 mg
Gelatin: 135.2 mg
Black soybean seed coat extract: 100 mg
Glycerin: 30.2 mg
Lecithin: 30 mg
Beeswax: 26 mg
Vitamin E: 20 mg Formulation Example 2: Tablet A tablet was prepared according to a conventional method using raw materials as cited below. As a black soybean seed coat extract, the black soybean seed coat extract prepared according to the method of Example 1 was used.

Dextrin: 179.69 mg
Black soybean seed coat extract: 100 mg
Reduced starch syrup: 28.56 mg
Crystalline cellulose: 26.51 mg
Calcium stearate: 5.25 mg
Fine silicon dioxide: 5.25 mg
Hydroxypropyl cellulose: 4.77 mg Formulation Example 3: Individually Packaged Stick Jelly An individually packaged stick jelly was prepared according to a conventional method using raw materials as cited below. As a black soybean seed coat extract, the black soybean seed coat extract prepared according to the method of Example 1 was used.
Rare sugar-containing syrup: 1000 mg
Black soybean seed coat extract: 100 mg
Gelling agent (thickening polysaccharide): 100 mg
Sweetener (xylitol, sucralose, thaumatin, acesulfame potassium): 70 mg
Flavor: 20 mg
Water: 8710 mg

INDUSTRIAL APPLICABILITY

The composition comprising a black soybean seed coat extract as an active ingredient of the present invention can improve an autonomic nervous system modulatory function and a cognitive function. Therefore, the composition for modulating an autonomic nervous system of the present invention and the composition for improving a cognitive function of the present invention are usable and useful in a wide range of fields including pharmaceuticals, quasi-pharmaceutical products, foods with functional claims, and supplements.

The invention claimed is:

1. A method for modulating an autonomic nervous system, comprising administering an effective amount of a black soybean seed coat extract to a subject in need thereof, wherein the black soybean seed coat extract is an extract of black soybean seed coat obtained by using water containing sulfuric acid as an extraction solvent,
wherein the black soybean seed coat extract contains 30% w/w or more of polyphenols, wherein the polyphenols include cyanidin 3-glucoside, proanthocyanidins, catechin and epicatechin collectively in an amount of 10% w/w or more of the black soybean seed coat extract, and
wherein the black soybean seed coat extract comprises a lower concentration of cyanidin 3-glucoside as compared to a total concentration of 2-mer to 9-mer proanthocyanidins.

2. The method according to claim 1, whereby mental fatigue, drowsiness, eyestrain, or shoulder stiffness is prevented or improved.

3. A method for improving a cognitive function, comprising administering an effective amount of a black soybean seed coat extract as a single effective component to a subject in need thereof, wherein the black soybean seed coat extract is an extract of black soybean seed coat obtained by using water containing sulfuric acid as an extraction solvent, and wherein the subject is a healthy subject and is subjected to a mental fatigue load,
wherein the black soybean seed coat extract contains proanthocyanidins, monomers of catechin and monomers of epicatechin collectively in an amount of 10% w/w or more of the black soybean seed coat extract, and
wherein the black soybean seed coat extract comprises a lower concentration of cyanidin 3-glucoside as compared to a total concentration of 2-mer to 9-mer proanthocyanidins.

4. The method according to claim 1, wherein the subject is subjected to a mental fatigue load.

5. The method according to claim 1, wherein the black soybean seed coat extract is administered in an oral composition.

6. The method according to claim 1, wherein the black soybean seed coat extract is administered in a food or beverage composition.

7. The method according to claim 3, wherein the black soybean seed coat extract is administered in an oral composition.

8. The method according to claim 3, wherein the black soybean seed coat extract is administered in a food or beverage composition.

* * * * *